United States Patent
Yodh et al.

[19]

[11] Patent Number: 5,917,190
[45] Date of Patent: Jun. 29, 1999

[54] OBJECT IMAGING USING DIFFUSE LIGHT

[75] Inventors: Arjun G. Yodh; Britton Chance; David A. Boas; Maureen O'Leary, all of Philadelphia, Pa.

[73] Assignee: Trustees of the University of Pennsylvania, Philadelphia, Pa.

[21] Appl. No.: 08/637,645

[22] PCT Filed: Oct. 31, 1994

[86] PCT No.: PCT/US94/12486
§ 371 Date: Jul. 25, 1996
§ 102(e) Date: Jul. 25, 1996

[87] PCT Pub. No.: WO95/12132
PCT Pub. Date: May 4, 1995

Related U.S. Application Data

[63] Continuation of application No. 08/145,466, Oct. 29, 1993, abandoned.

[51] Int. Cl.[6] .................................................... G01N 21/17
[52] U.S. Cl. ........................................ 250/458.1; 356/275
[58] Field of Search .......................... 356/375; 250/458.1

[56] References Cited

FOREIGN PATENT DOCUMENTS 62-124443  6/1987  Japan ...................................... 356/375

*Primary Examiner*—Constantine Hannaher
*Attorney, Agent, or Firm*—Michael P. Dunnam

[57] ABSTRACT

Imaging tumors using diffuse light. An imaging system includes a source of diffuse light for generating oscillatory diffuse photon density waves to illuminate an object, a detector for detecting diffuse photon density waves interacting with the object, and a computer interfaced with the detector for processing data corresponding to the photon density waves detected to determine at least a position of the object. In one embodiment, the turbid medium and the object have associated therewith at least one diffusion coefficient and the diffuse photon density waves which illuminate the object refract around the object as a result of their interaction with it, thereby producing a distorted wavefront that allows the computer to construct an image of the object. In another embodiment, a fluorescent object produces re-radiated diffuse photon density waves which allow the object to be imaged.

40 Claims, 10 Drawing Sheets

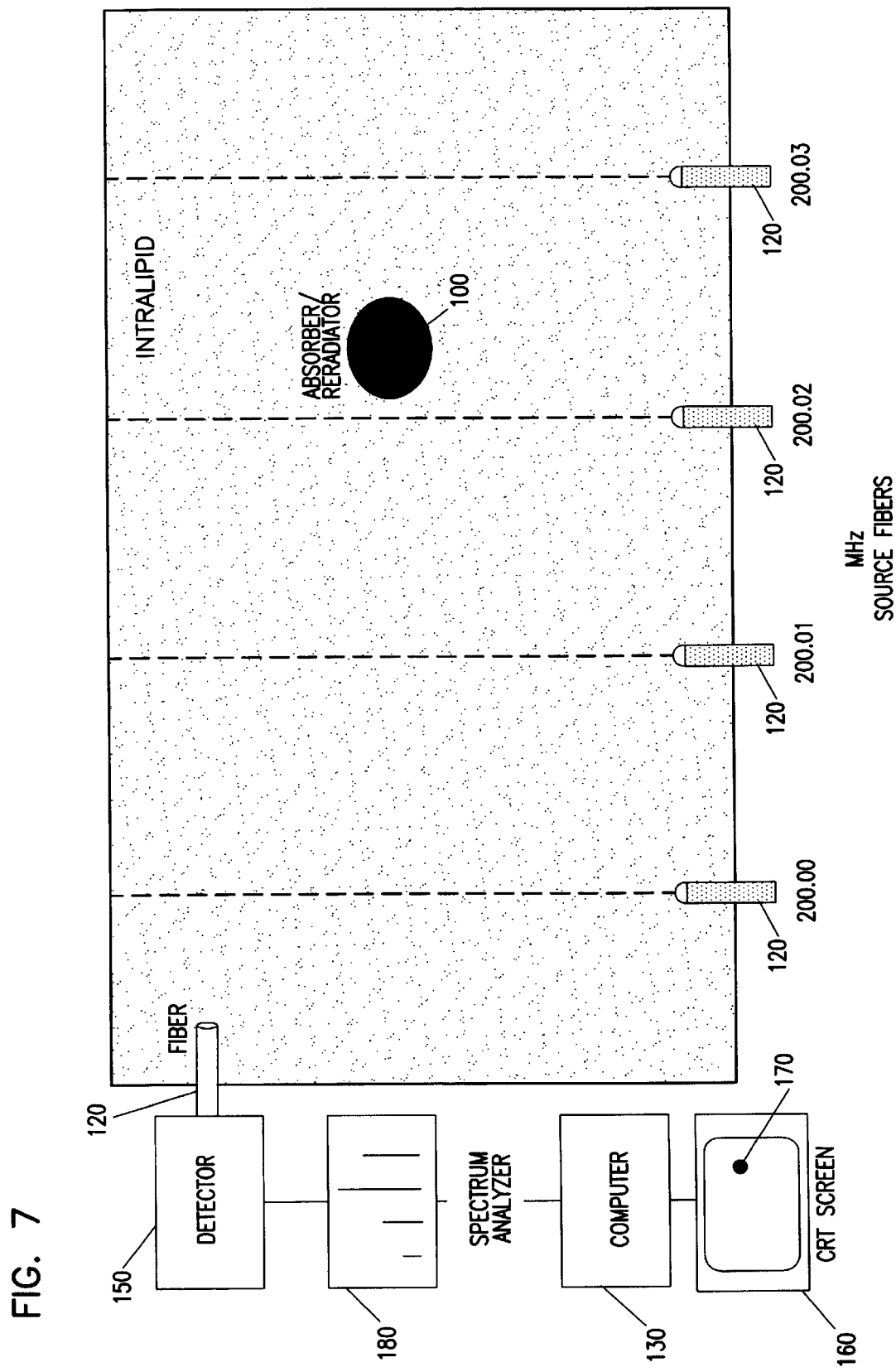

OBJECT IMAGING USING DIFFUSE LIGHT

CROSS-REFERENCE TO RELATED APPLICATIONS

This application is a United States National Phase Application of PCT/US94/12486 filed Oct. 31, 1994 which is a continuation of U.S. application Ser. No. 08/145,466 filed Oct. 29, 1993, (now abandoned).

FIELD OF THE INVENTION

This invention relates generally to imaging of objects. More specifically, this invention relates to methods and apparatus for imaging objects using diffuse light.

BACKGROUND OF THE INVENTION

Techniques for imaging objects have been used for nearly a century in the medical arts for diagnosing and understanding the myriad diseases and maladies that afflict the human body. Imaging techniques have also found use in such diverse fields as radio astronomy, sonar, radar and other fields which require information about an object which is not readily visible to the naked eye and therefore not easily examined. Medical imaging techniques include, for example, X-ray imaging, positron emission tomography (PET), ultrasound imaging and the well known magnetic resonance imaging (MRI).

In all of the imaging techniques mentioned above, narrow band frequency radiation illuminates the object of interest to produce reflected or emitted radiation which is then gathered from the object by a detector. The reflected or emitted radiation is then processed by an imaging algorithm to obtain useful information about the object.

In medical applications, the use of ionizing radiation in imaging, for example with X-rays, involves significant health risks to a patient when the patient is exposed to the radiation for prolonged periods of time or in multiple imaging schemes. Furthermore, certain of these imaging techniques undesirably involve the use of invasive procedures which are both costly and painful. Yet other techniques such as MRI do not yield consistently useful clinical results.

There has thus arisen in the medical imaging art an interest in developing non-invasive, safe and relatively fast techniques which can take advantage of the natural scattering of visible and infrared light through media containing objects to be imaged. Techniques using diffuse light could be used in conjunction with other imaging schemes such as X-ray imaging or MRI to produce highly useful clinical images for diagnostic purposes.

Much of the progress in imaging with diffusive light has focused on ballistic techniques using lasers. With these techniques, an intense pulsed laser illuminates a sample. By time gating photons that have been scattered only a few times and rejecting all other photons, the optical absorption of the medium and objects found therein can be mapped. This technique works best when the allowed time window is short and the photons deviate the least from their "ballistic" trajectory. Unfortunately, the transmittal intensity of unscattered photons diminishes exponentially with increasing sample thickness.

Because of the limitations of ballistic imaging, it is difficult to obtain high quality images of relatively thick objects with low power lasers. Examples of ballistic imaging techniques are disclosed in K. M. Yoo, F. Lie and R. R. Alfano, *Optics Letters,* Vol. 16, p. 1068 (1991), and in D. A. Benaron and D. K. Stevenson, *Science,* Vol. 259, p. 1463 (1993).

A second technique for imaging using diffuse light is optical phase modulation. Phase modulation techniques have permitted the location of single absorbers using low power, continuous wavelength lasers. In accordance with these techniques, an amplitude modulated source creates photon density waves that acquire anomalous phase shifts due to the absorber. For the case of a single absorber, the distortions are readily interpreted; however for a more complicated object a general analysis is required.

An example of imaging with diffuse light is disclosed in U.S. Pat. No. 5,119,815, Chance where scattered light was applied to a biological imaging application. The Chance patent discloses a technique for solving the diffusion equation for a homogeneous medium to obtain the overall optical absorption characteristics. This was possible for the homogeneous medium because the long time limit of the logarithmic derivative of the detected intensity yields the absorption characteristics directly. Thus the absorption characteristics for uniform structures may be obtained with the methods and apparatus disclosed in the Chance patent.

Still other attempts to image with diffuse light are disclosed in U.S. Pat. No. 5,070,455, Singer et al. In the Singer et al. system, light intensities are measured at many sensor positions (pixels), initial values of absorption or scattering coefficients are assigned at each pixel, and then a new set of intensities at each pixel is calculated. The calculated intensities are compared to the real intensities, and the intensity differences are used to generate a subsequent interaction of absorption or scattering values for each pixel.

The methods described in Singer et al. usually require many iterations since the absorption or scattering values may not converge rapidly. Furthermore, the Singer et al. system utilizes cumbersome Monte-Carlo statistical techniques which consume large amounts of processing time without guaranteeing computational success. Singer et al.'s methods may also produce false local minima providing misleading results for the absorption characteristics.

Thus prior imaging techniques using diffuse light for scattering fail to solve a long-felt need in the art for robust imaging techniques which can produce reliable images in biological systems. Solution of the aforementioned problems has heretofore eluded the medical imaging art.

SUMMARY OF THE INVENTION

The aforementioned deficiencies in the imaging art are overcome by methods and apparatus provided in accordance with the present invention which provide imaging of objects in turbid media using diffuse light.

In a preferred embodiment of the invention an imaging system comprises source means for generating oscillatory diffuse photon density waves to illuminate the object, detection means for detecting diffuse photon density waves produced as a result of the diffuse photon density waves interacting with the object, and processing means interfaced with the detection means for processing data corresponding to the photon density waves detected by the detection means to determine at least a position of the object. The turbid medium and the object have associated therewith at least one diffusion coefficient and the diffuse photon density waves which illuminate the object diffract around or refract through the object as a result of their interaction with it, thereby producing a distorted wavefront such that after the detection means detects the distorted wavefront the processing means determines the diffusion coefficient of the turbid medium and the object. More preferably, the processing means constructs phase and amplitude contours corresponding to propagation of the distorted wavefront and further determines at least the position of the object from the phase and amplitude contours, thereby imaging the object.

In yet a further preferred embodiment of imaging systems provided in accordance with the invention, display means are interfaced with the processing means for displaying the image of the object, the source means comprises at least one laser, and the detection means comprises an optical fiber interfaced with a photomultiplier tube.

Further aspects of the invention provide imaging of a fluorescent object such that the diffuse photon density waves having a first wavelength cause the object to fluoresce, thereby producing re-radiated diffuse photon density waves having a second wavelength such that after the detection means detects the re-radiated diffuse photon density waves, the processing means can image the object.

In the embodiment of the invention where fluorescent, re-radiated diffuse photon density waves are detected, the source means preferably comprises a plurality of lasers oriented around the object which alternately irradiate the object with the diffuse photon density waves of the first wavelength to cause the object to fluoresce. The detection means comprises an optical fiber that is placed in proximity to the object and a photomultiplier tube interfaced to the optical fiber. The imaging system further comprises switch means interfaced with each of the plurality of lasers for alternately and sequentially turning on and off each laser, and radio frequency driving means interfaced through the switch means with the lasers for driving the lasers to produce the diffuse photon density waves of the first wavelength.

Alternatively, the imaging system comprises a plurality of lasers each having a spatial location with respect to the object. Each laser is more preferably modulated at all times during imaging at a different frequency in a frequency range around a specified frequency, thereby producing a power spectrum associated with each spatial location around the object. Analysis means are provided interfaced with the detection means and the processing means for analyzing the power spectrums associated with each spatial location to determine the position of the object.

In still a further preferred embodiment of imaging systems which take advantage of fluorescent, re-radiated diffuse photon density waves, the source means comprises a phased-array. The phased-array, preferably comprises at least two lasers that are substantially one hundred and eighty degrees out of phase with each other, thereby producing the diffuse photon density waves having the first wavelength which interfere destructively to produce an amplitude null line and a substantially one hundred and eighty degree phase shift across the null line equidistant from the lasers. By scanning the null line with the phased-array the processing means can produce an image of the object in the turbid medium.

Systems and methods provided in accordance with the present invention will provide efficient imaging of tumors and other maladies that effect human tissue. These systems will also prove to be much more economical to build when compared to prior imaging systems, since they will not require the complex machinery that is associated with prior imaging systems such as MRI. Furthermore, since the methods and apparatus provided in accordance with the present invention utilize diffuse light for imaging, more reliable images of tumors will be presented to the medical diagnostician or clinician so that cancerous tumors and other inhomogeneities in the tissue will be detected earlier and more readily. This holds the promise of saving lives and reducing the overall costs of medical care.

The features, objects and advantages of the invention will be understood by those with skill in the art from the following detailed description of the preferred embodiments thereof when read in conjunction with the drawings which are first described briefly below.

BRIEF DESCRIPTION OF THE DRAWINGS

FIG. 7 is a schematic representation of a "frequency-encoded" system for imaging diffuse photon density waves re-radiated from a fluorescent object.

DETAILED DESCRIPTION OF PREFERRED EMBODIMENTS

Figure 1:
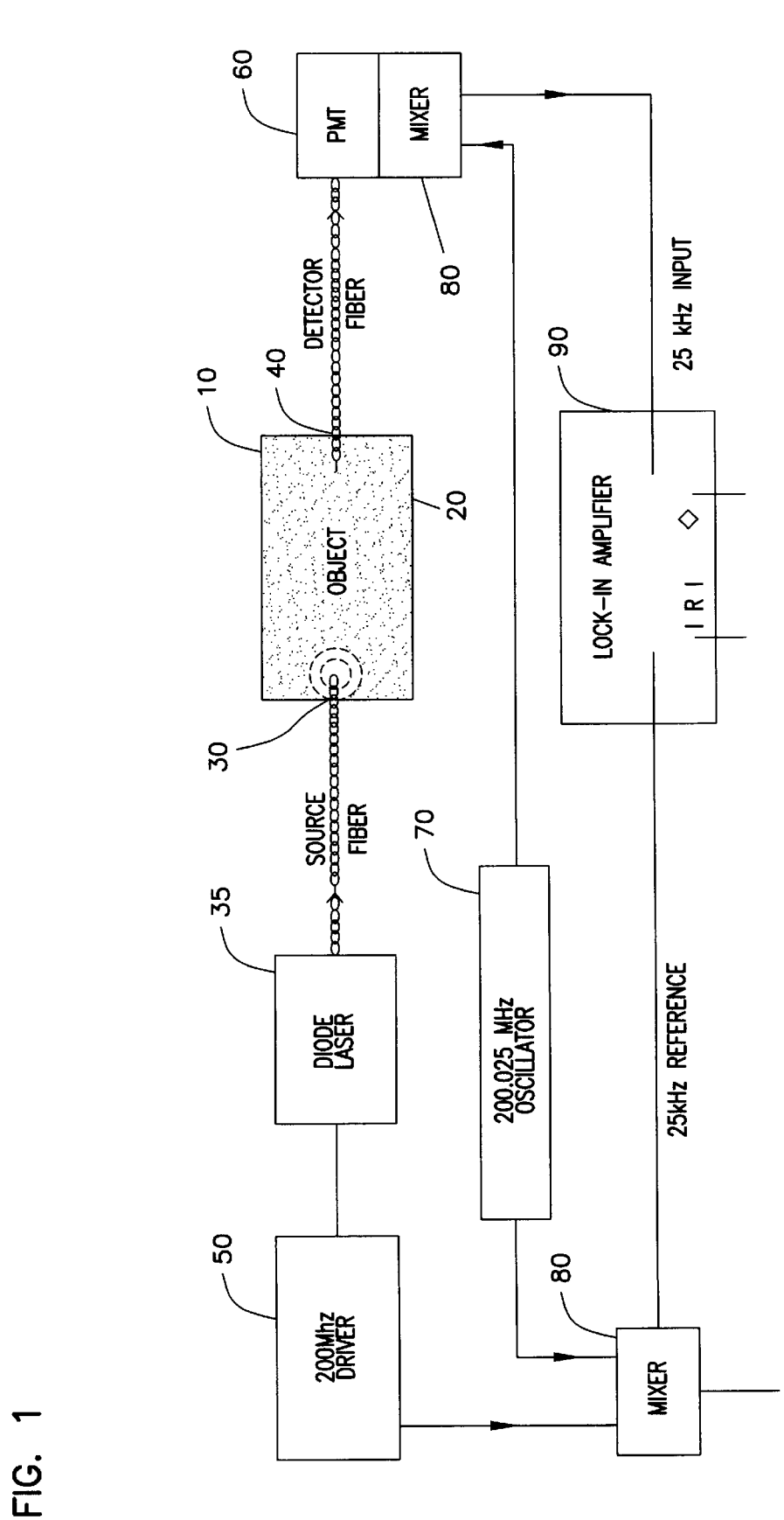
FIG. 1 is a schematic representation of an imaging system using diffuse light wherein scattering experiments with diffuse photon density waves occurs.

Propagating disturbances are produced in a dense, turbid medium containing objects when amplitude modulated light sources are introduced into the turbid medium. In biological and medical imaging applications, human tissue, such as breast tissue containing tumors, is such a turbid medium containing objects to be imaged. In accordance with the present invention, an oscillatory light source introduces diffuse photon density waves (hereinafter referred to as "DPDW") in the turbid medium. While the results described herein have been achieved with respect to several experimental apparatus to be described hereafter, those with skill in the art will immediately recognize that the techniques and apparatus disclosed are readily applicable to imaging human body tissue which is infected with tumors or other maladies that will appear as inhomogeneities in the tissue which is a turbid medium.

The inventors of the subject matter herein claimed and disclosed have discovered that DPDW can be used in at least two ways to perform imaging. In a first preferred embodiment, DPDW are introduced into a turbid medium and refracted through and diffracted around objects in the medium, thereby producing a distorted wavefront which can then be analyzed to yield useful information concerning at least a position and size of the object around which the DPDW have been refracted.

In a further preferred embodiment, the inventors have determined that by introducing fluorescence to the object, photons in the re-radiated DPDW will be emitted from the object at a shifted wavelength with respect to the original DPDW and the re-radiated DPDW then analyzed to determine at least the position of the fluorescent objects in the turbid medium. This is particularly useful for imaging of tumors since in prior, non-diffuse light imaging techniques fluorescent dyes which respond to various forms of radiation have typically been introduced into tumors, thereby yielding information about the location and size and nature of the tumor under examination.

Thus, imaging tumors and objects in turbid media with diffuse light will in the future produce significant and effective images for diagnostic and clinical purposes.

I. The Basic Theory of DPDW Propagation in a Turbid Medium

The basic mechanics of wave propagation in a turbid medium have been explored by the inventors when performing imaging in accordance with the present invention. DPDW are scalar, over-damped, traveling waves of light energy density, denoted U(r,t). They propagate through any medium in which the transport of light energy density, U, is governed by the "diffusion equation," which is $$\frac{\partial U}{\partial t} = D\nabla^2 U$$

where D is the "diffusion coefficient" for the medium. This diffusion equation holds for a non-absorbing medium. Some examples of optically turbid media include dense suspensions of micrometer-sized spheres, human tissue, paints, foams, and Intralipid (a mixture of water, soybean oil and egg yolk). The introduction of amplitude modulated light into a turbid medium produces a macroscopic ripple of brightness that is microscopically composed of individual photons undergoing random walks. The disturbances arise whenever the diffusive system is driven by an oscillating source.

The oscillatory part of the solution for an infinite, non-absorbent, homogeneous turbid medium in the presence of a point source located at the origin follows the form:

$$U(r,t)=(A/Dr)(\exp\{-kr\})(\exp\{i(kr-\omega t)\})$$

where A is a constant, r is the radial distance from the origin, D is the diffusion coefficient for light in the medium, ω is the source modulation frequency, and $k=(\omega/2D)^{1/2}$. Although the wave is very rapidly attenuated, it has a well-defined wavelength, amplitude and phase at all points. Interestingly, the wavelength can be altered by modifying D or ω.

When absorption is present, a similar solution to Equation (1) can be obtained, but the real and imaginary parts of the wave vector k are different and depend explicitly on the sample absorption length (as well as the photon random walk step for inverse scattering factor). The macroscopic disturbance obeys a Helmholtz equation, and therefore has many properties that are normally associated with conventional electromagnetic radiation. Thus, DPDW display refraction, diffraction, and interference properties similar to those observed with conventional electromagnetic radiation propagating through media. By examining the energy contours produced as a result of the interaction of the DPDW with the objects in the medium according to the techniques of the present invention, the objects can be imaged to obtain useful clinical data.

II. Imaging Using Refracted DPDW

In a preferred embodiment, an apparatus for imaging objects in a turbid medium is shown schematically in FIG. 1. The object 10 may contain smaller objects such as tumors which must be characterized for clinical purposes. For experimental purposes, the dense turbid medium imaged is Intralipid, a polydisperse suspension of particles having an average diameter of ~0.4 μm, but a relatively wide range of sizes (i.e., from ~0.1 to ~1.1 μm). By changing the solution concentration of the Intralipid, it is possible to vary the light diffusion coefficient, D, of the medium. The photon transport mean free path l* was about 0.2 cm in a 0.5% concentrated solution.

To perform imaging of the smaller objects in the Intralipid, a large fish tank 20 (30 cm×30 cm×60 cm) is filled with this material. When the absorption is very small, the suspensions in the Intralipid are dilute, and therefore the diffusion coefficient is inversely proportional to the Intralipid concentration.

In a preferred embodiment, a source fiber 30 and detector fiber 40 (both ~4 mm in diameter) are placed in proximity to object 10. The source light 30 is preferably derived from a 3-mW diode laser 35 operating at about 816 nm. The diode laser 35 is amplitude modulated at 200 MHz by driver 50, and the position of the source fiber 30 is fixed. The detector fiber 40 is in detecting proximity to the object 10 and is further connected to a photomultiplier tube 60 on its other end. In order to facilitate phase and amplitude measurements, both the reference from the driver 50 and the detected signal are down-converted to 25 kHz by heterodyning with a second oscillator 70 to 200.025 MHz. Mixers 80 preferably combine the frequencies to produce the 25 kHz signals shown. The low-frequency signals are then measured using a lock-in amplifier 90.

In a more preferred embodiment, the phase shift (and ac amplitude) of the detected light is measured with respect to the source 30 at each point on a 0.5-cm square planar grid throughout the sample. Constant phase contours are then determined by linear interpolation of the grid data. The sensitivity of the apparatus shown in FIG. 1 is about $10^5$. Since the signal amplitude decays by $<e^{-2\pi}$ in one wavelength, the range of the apparatus is limited to slightly more than one wavelength. Nevertheless, it is possible to clearly distinguish the essential physical phenomena of the DPDW scattering through the object 10 with this apparatus.

The results obtained by imaging with the system of FIG. 1 demonstrate that a "diffusional index of refraction" exists for DPDW, and that it is possible to manipulate the diffusional index of refraction by controlling the photon diffusion coefficients (D) of adjacent turbid media. This is of considerable importance in biological systems, where the natural curvature of organs such as the brain, heart, or kidney, together with changes of scattering and absorption as in the grey-white matter transition of the brain, can lead to significant modifications of the trajectories of diffuse photons.

Figure 2:
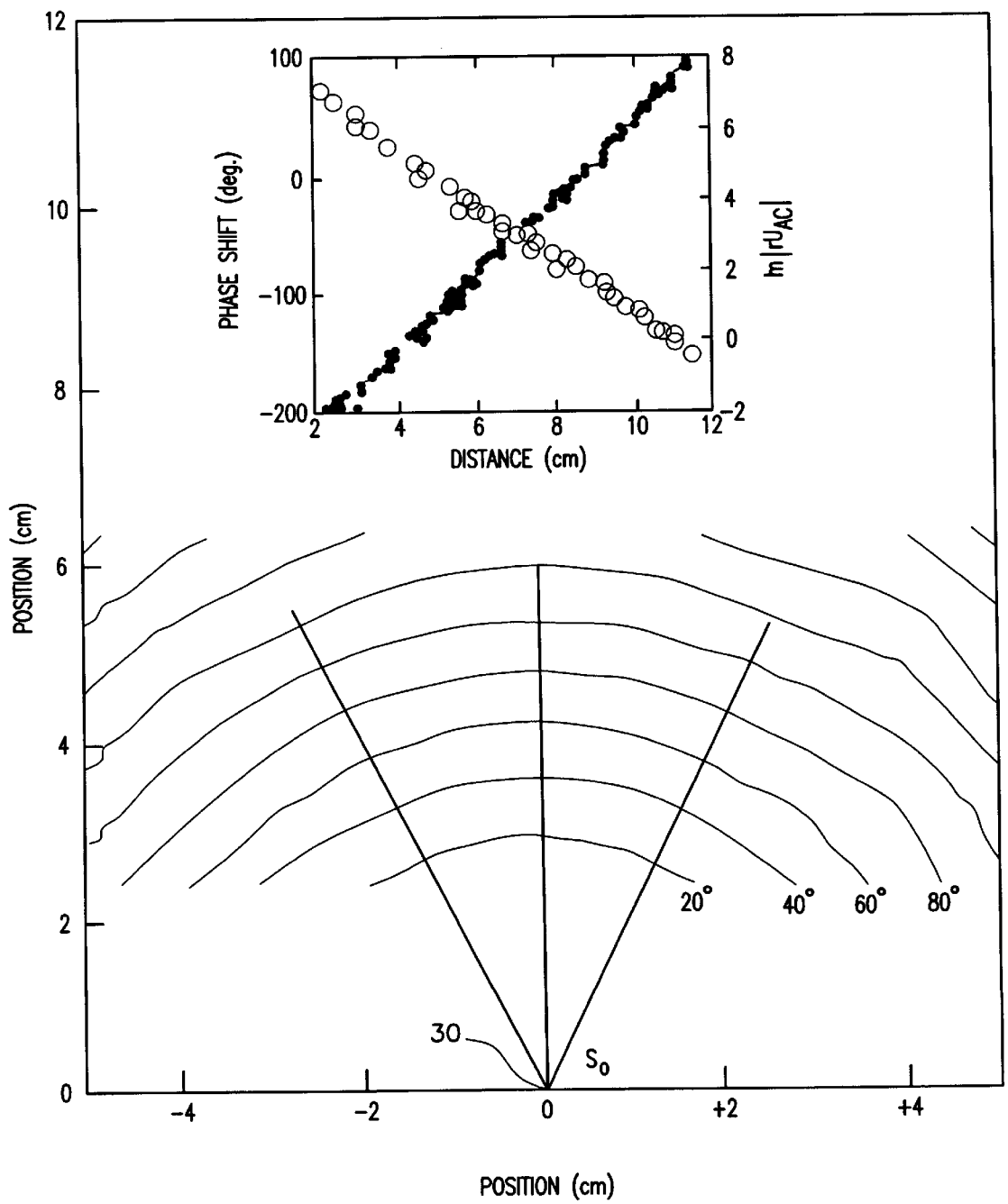
FIG. 2 depicts measured constant contours of diffuse photon density waves propagating through a turbid medium.

Results for a ~0.5% concentrated homogeneous turbid medium are illustrated in FIG. 2. Constant phase contours are shown at 20° intervals about the source. The contours are approximately circular, and their radii can therefore be extrapolated back to the source 30. In the insert of FIG. 2, the phase shift and the quantity $\ln|rU_{ac}(rt)|$ as a function of radial distance from the source are plotted. From these measurements it is possible to determine that the wavelength of the DPDW is 11.2 cm, the photon transport mean free path is ~0.2 cm, and the photon absorption length is ~52 cm in ~0.5% Intralipid at 22° C. In this case, the photon absorption can be attributed almost entirely to water.

Figure 3:
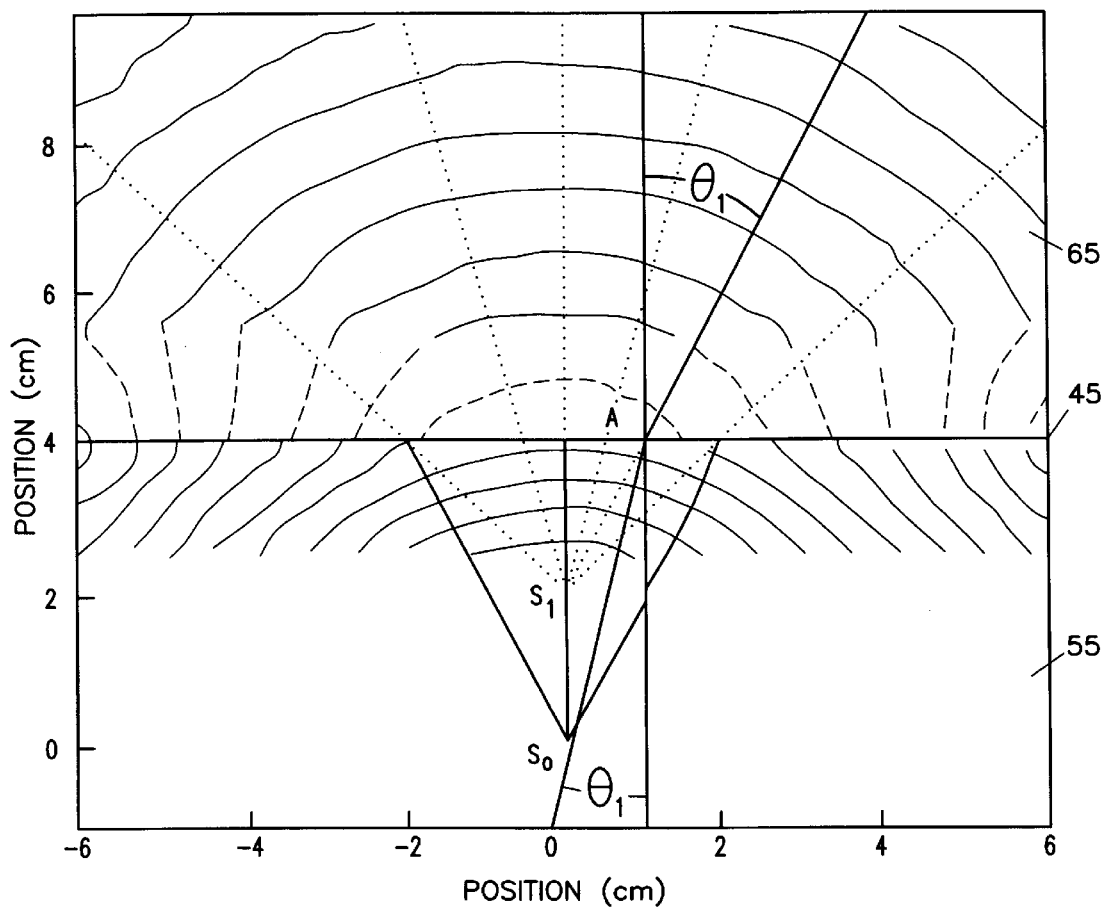
FIG. 3 depicts measured constant phase contours of diffuse photon density waves propagating through turbid media and refracting across a plane boundary between two turbid media with different light diffusion coefficients.
Figure 4:
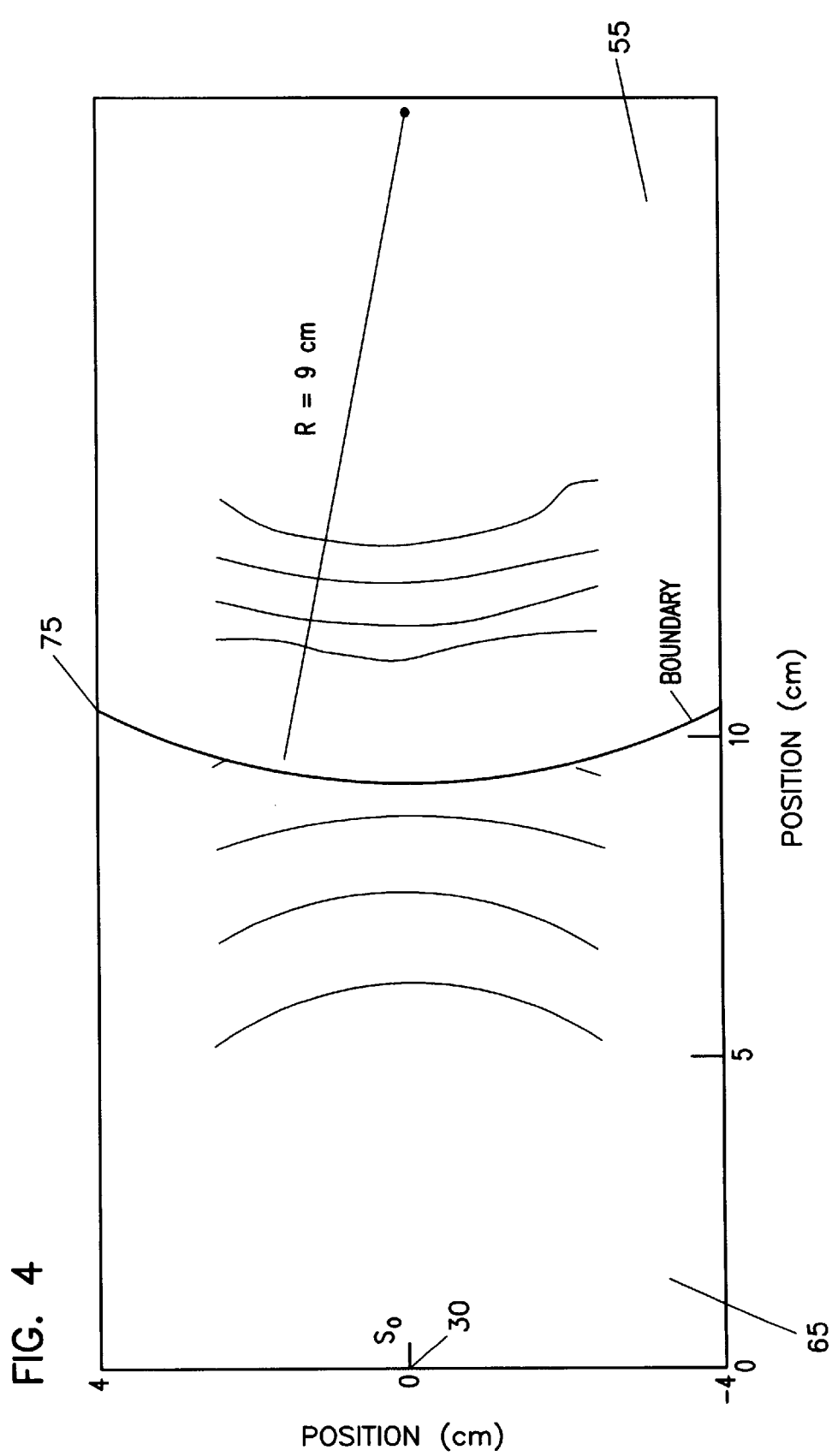
FIG. 4 is a graph of phase contours of diffuse photon density waves propagating through turbid media after refracting across a cylindrical boundary separating two turbid media wherein lensing effects are observed.

Referring to FIGS. 3 and 4, refraction of the DPDW is shown in three ways: (1) when a plane, acrylic partition or (2) a cylindrical acrylic partition is placed in the tank to simulate a boundary, and (3) when no partition is in place so that the medium is homogeneous. In FIG. 3, constant phase contours exist at about every 20°. When the plane boundary 45 is introduced, the lower medium 55 has a concentration, $c_l$, ~1.0% and light diffusion coefficient $D_l$. The upper medium 65 has a concentration, $c_u$, ≈0.25% and light diffusion coefficient $D_u$. The contours below boundary 45, shown at the 4 cm position on the y-axis, are just the homogeneous media contours without refraction. These contours are obtained before the partition is introduced. The contours above the boundary 45 are derived from the DPDW that are transmitted into the less concentrated medium.

Theory predicts that the wavelength in the less dense medium, $\lambda_u$, is 14.8 cm, and should be greater than the wavelength of the DPDW in the incident medium, $\lambda_l$, which is 8.17 cm. The ratio of the two wavelengths should equal the ratio of the diffusional indices of refraction of the two media. As is predicted, $\lambda_u = \lambda_l (D_l/D_u)^{-1/2} \sim \lambda_l (c_l/c_u)^{1/2}$.

Theory also predicts that the apparent source position $S_i$, as viewed from within the upper medium 65, should be shifted from the real source position, $S_o=4.0\pm0.2$ cm, by a factor $\lambda_l/\lambda_u=0.55$. This is verifiable from the data of FIG. 3 since, using the radii from the full contour plots, the apparent source position is shifted from 4.0±0.2 to 2.0± 0.25 cm.

In accordance with the invention, FIG. 3 explicitly demonstrates Snell's law for DPDW. This can be seen by following the ray from $S_o$ to the point A at the boundary 45, and then into the upper medium 65. The ray in the lower medium 55 makes an angle $\theta_i=14°$ with respect to the surface normal. The upper ray is constructed in the standard way between the apparent source position $S_i$, through the point A on boundary 45, and into the medium 65 above the boundary. The upper ray is perpendicular to the circular wave fronts in the less dense medium 55, and makes an angle $\theta_r=26.6°$ with respect to the boundary normal. Therefore, it can be seen graphically that $\sin\theta_i/\sin\theta_r = 0.54 \approx \lambda_l/\lambda_u$, so that Snell's law accurately describes the propagation of DPDW across boundary 45.

The inventors have also determined that by using a circular boundary (shown generally at 75 in FIG. 4) to separate the two turbid media, the curvature of the DPDW can be altered in analogy with a simple lens in optics. Referring to FIG. 4, two semi-infinite media are separated by curved boundary 75, and the medium 55 on the right is more concentrated. The constant phase contours of the transmitted wave exhibit a shorter wavelength, and are clearly converging toward some image point to the right of the boundary. The medium 65 on the left ($\lambda_l$) has an Intralipid concentration of ~0.1%, and the medium 55 on the right ($\lambda_r$) has a concentration of ~1.6%.

The wavelength ratio is measured to be $\lambda_r/\lambda_l=3.8\pm0.3$. The curved surface 75 has a radius $R=9.0\pm0.4$ cm. The position of source 30 is $S_o=9.4\pm0.3$ cm. The image position is determined to be $S_i=12\pm2$ cm. This result deviates somewhat from the well-known paraxial result from geometrical optics for imaging by a spherical refracting surface. The deviation is primarily a result of spherical aberration. However, in accordance with the invention, the curvature of the wave fronts is reversed after traversing the circular boundary 75.

The results shown in FIGS. 2, 3 and 4 which are obtained from the apparatus of FIG. 1 show that it is possible to exert substantial control over the transport of diffuse light in dense random media. The inventors have clearly demonstrated that the index of refraction of DPDW in such a medium depends on the photon diffusion coefficient or random walk step of the photons in the medium. This allows imaging of inhomogeneities in the medium by examining the DPDW, a result that has not heretofore been achieved in the art.

It should be noted that when deriving Equation (1), the differential form of Fick's law and photon flux conservation principles were used. In a preferred embodiment of imaging by examining the scattering and diffraction refraction of DPDW, the effects of absorption of the DPDW can be ignored, and it can be assumed that the time it takes for light to travel a single random walk step is much shorter than the modulation period. In this case, the oscillatory part of the light energy density $U_\omega(r)$ obeys the Helmholtz equation, i.e., $(\overline{\nabla}^2+k^2)U_\omega(r)=0$. The only significant difference of DPDW propagation in comparison to conventional wave phenomena is that $k^2=i(\omega/D)$, and therefore k is complex.

The spatial part of $U_{ac}(r,t)$ in Equation (1) is simply the Green's function solution of the Helmholtz equation with the appropriate k. Therefore, some of the basic theorems that apply to solutions of the Helmholtz equation will apply to DPDW propagation in a turbid medium. For example, a Kirchoff integral can be constructed for these waves using the Green's function solution. This provides a formal method by which to calculate the wave amplitude and phase at various distances from a "diffracting" aperture as has been discussed in this Part II. To the extent that the Kirchoff integral embodies the basic Huygens-Fresnel principle, contributions of different elements of a scattering surface arising from damped, spherical point sources will be observed. This also implies that the focusing of DPDW will have the same limitations due to diffraction as in the case of light propagating in a standard optical medium. Thus, imaging of tumor-like inhomogeneities in tissue can be accomplished in accordance with the present invention by examining the refractive, diffractive and scattering properties of DPDW incident to the tissue.

III. Imaging by Examining Re-Radiated DPDW

The inventors of the subject matter herein claimed and disclosed have also discovered that examining re-radiated DPDW from a fluorescent inhomogeneity in a turbid medium provides methods of imaging inhomogeneities in the medium. Many types of tumors which occur in the human body comprise inhomogeneities which can be made to fluoresce after being irradiated with DPDW, and therefore, the inventors have determined that re-radiated DPDW provide an excellent means of locating tumors.

In order to observe re-radiated DPDW and image an object, the model biological material Intralipid is used. An amplitude modulated 200 MHz or 50 MHz laser diode ~3 mW, 780 nm is fiber-coupled into the medium, and another optical fiber is used to detect diffuse photons as a function of position within the medium. Using the standard heterodyne techniques discussed earlier, the phase and amplitude of the DPDW in the medium can be observed.

Figure 5:
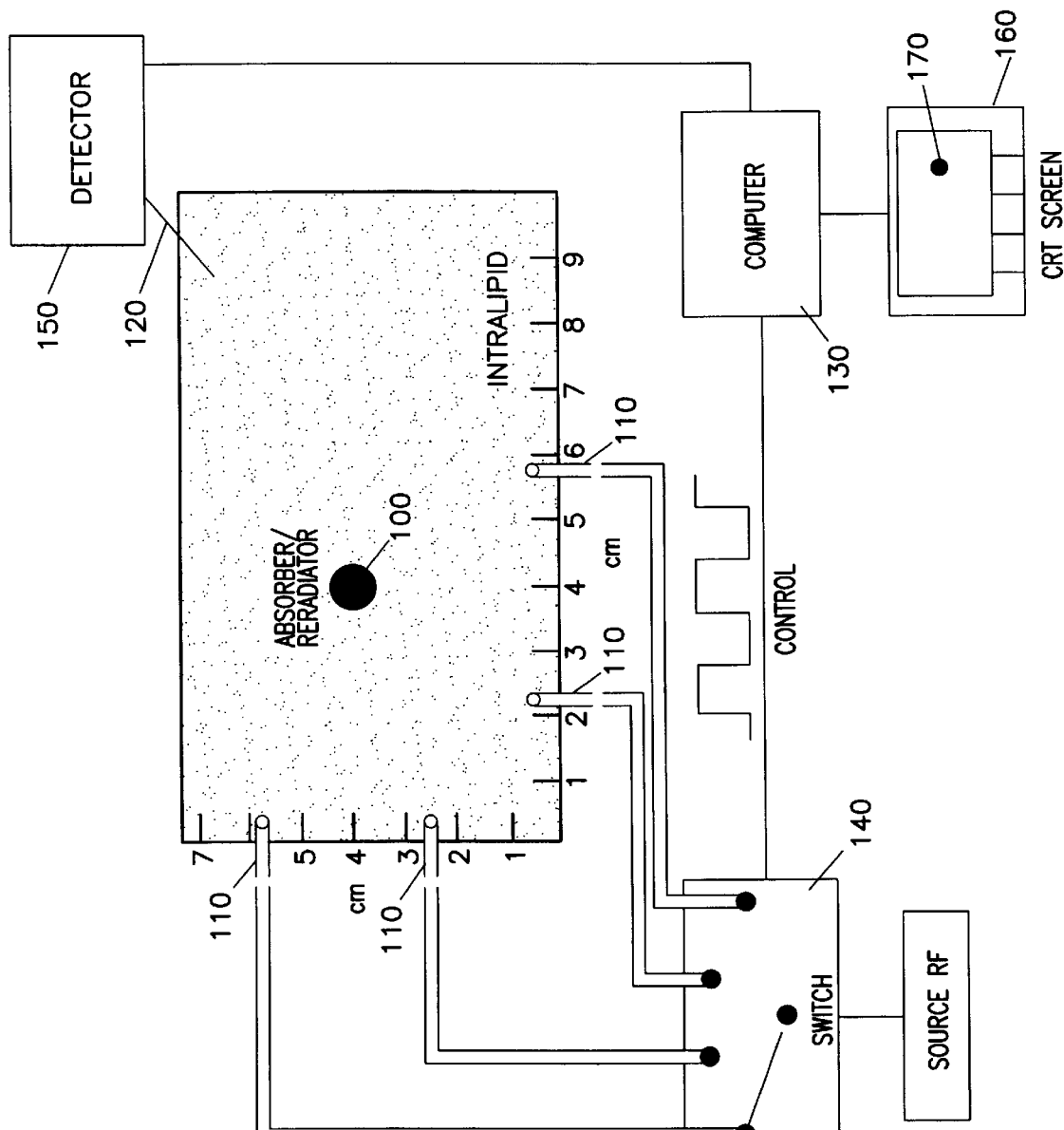
FIG. 5 is a schematic representation of a "time-sharing" system for imaging diffuse photon density waves re-radiated from a fluorescent object.

A preferred apparatus for imaging inhomogeneities in turbid media by detecting re-radiated DPDW is shown schematically in FIG. 5. The absorber/radiator shown at 100 preferably comprises a shell filled with Intralipid at a concentration of 0.4 mg/L Indocyanine green dye which is less than one tenth of the concentration commonly used in human subjects to test hepatic function. In this embodiment, multiple sources 110 and a single detector 120 are used to determine the center of the fluorescent object 100.

Computer processor 130 preferably outputs a control signal to switch 140 which controls the sequential activation of each of sources 110. A detector 150 which most preferably comprises a photomultiplier tube is interfaced both to detector fiber 120 and computer processor 130. In a further preferred embodiment, detector 150 is a Hamamatsu R928 or R1645u photomultiplier tube which also comprises a high voltage power supply that ensures adequate gain to computer processor 130 so the computer processor 130 can process the data received from detector fiber 120. A display device 160, preferably a CRT screen, is interfaced to computer processor 130 and outputs an image 170 of object 100.

To obtain image 170, a fluorescent object 100 is irradiated with multiple sources 110 of DPDW. It is then preferred to measure the amplitude (or phase) of the re-radiated light. The partial amplitude resulting solely from source i, is dependent on the $i^{th}$ source-object separation, the quantum efficiency of the dye in the object 100, and the object 100-detector 120 separation. Therefore:

$$|U_i| \propto \xi \frac{\exp(-k|\vec{r}_i - \vec{r}_o|)}{|\vec{r}_i - \vec{r}_o|} \frac{\exp(-k'|\vec{r}_o - \vec{r}_d|)}{|\vec{r}_o - \vec{r}_d|}, \qquad (2)$$

where $\xi$ is the quantum efficiency of the dye, $\vec{r}_i$ is the position of the $i^{th}$ source, $\vec{r}_o$ is the position of the object center, $\vec{r}_d$ is the detector position, and k (k') is the wave vector magnitude of the DPDW at 780 nm (830 nm).

The individual sources 110 are separately turned on and off, and the re-radiated amplitude for each object separation is measured. Since the source positions $\vec{r}_i$, and the detector position $\vec{r}_d$ are known, it is possible to estimate the object's position by finding the value of $\vec{r}_o$ that gives the best agreement with the measured ratio $|U_i|/|U_j|$. Generally, three sources 110 are necessary to localize the object in two dimensions. However, it is more preferable to use four or more sources to improve the signal-to-noise ratio of the imaging system. Using four sources 110 as shown in FIG. 5, it is possible to localize the center of the 1 cm spherical object 100 to within 0.4 cm. This two-dimensional localization is easily extended to three dimensions, as will be recognized by those with skill in the art.

Figure 6A:
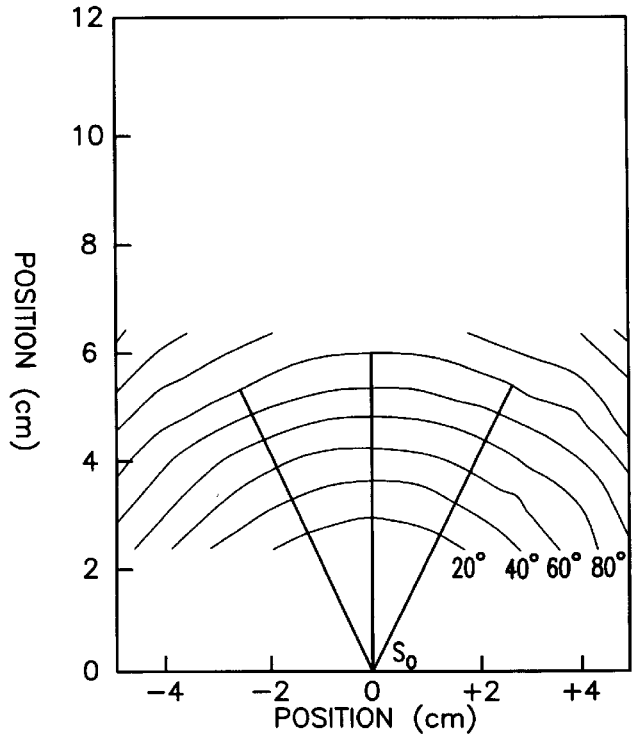
FIG. 6A is a graph of phase contours of the disturbance produced by a fiber point source in a turbid medium.

Referring to FIG. 6A, constant phase contours of the disturbance produced by the fiber point source located at the origin of the system are illustrated. In a more preferred embodiment, re-radiated DPDW are obtained by filling a spherical glass shell with the absorbing dye Indocyanine green, and then illuminating the sphere with DPDW in the Intralipid solution. The dye is preferably chosen to absorb radiation at the source wavelength of 780 nm, and very soon thereafter re-radiate photons at a red-shifted energy, 830 nm. Because the dye has a lifetime of less than 1 nsec compared to the 5 nsec period of the source, the re-radiated energy is in the form of a DPDW at the red-shifted energy.

Figure 6B:
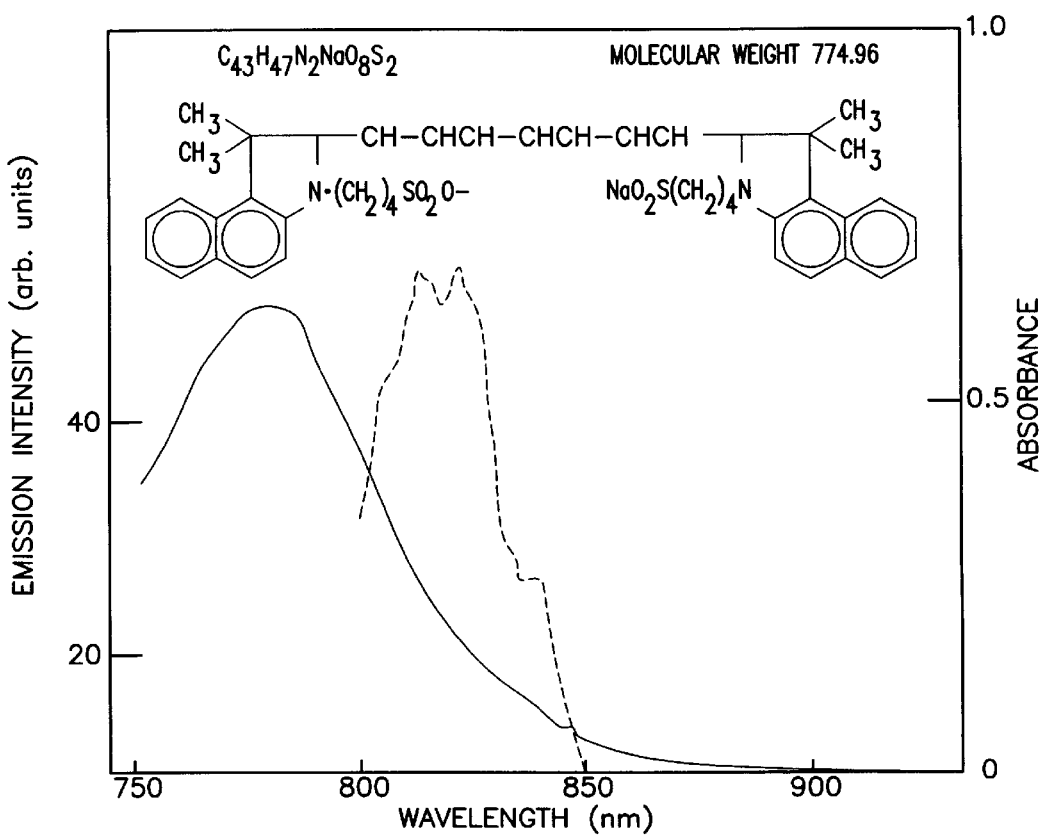
FIG. 6B is a graph of the absorption and emission characteristics of a fluorescent dye contained in a spherical shell within the turbid medium.
Figure 6C:
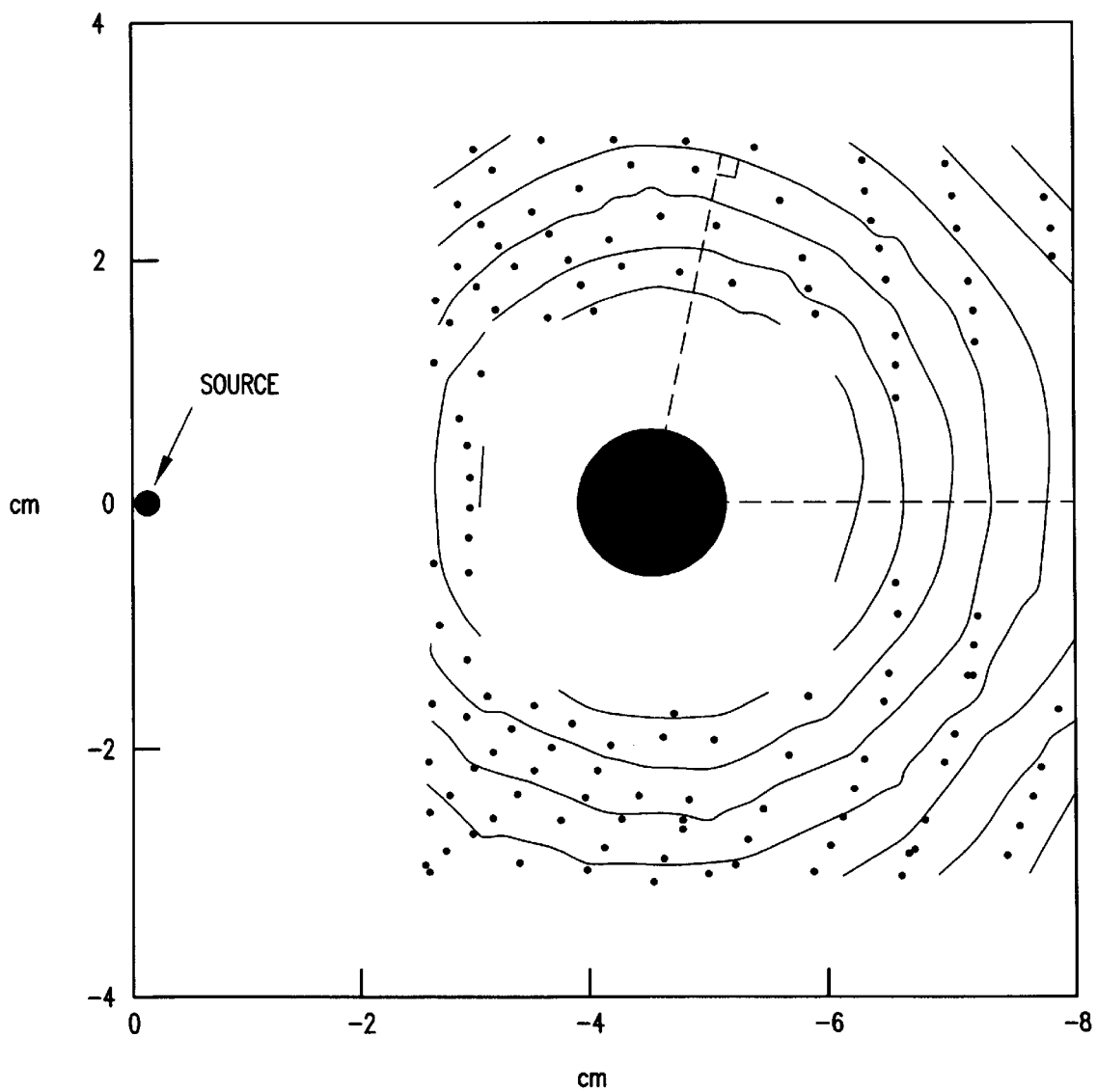
FIG. 6C is a graph of measured constant amplitude phase contours for diffuse photon density waves emitted from a source into a turbid medium, and re-radiated diffuse photon density waves.

The absorption and emission characteristics of the dye are shown in FIG. 6B wherein the inset is the chemical formula of the dye material. The Intralipid solution surrounding the obstacle has a concentration of 0.1% giving a source diffuse photon density wavelength of ~18 cm. A point source at the origin generates the incident DPDW. Constant amplitude contours of the incident wave in the presence of the obstacle are shown in FIG. 6C (dashed lines). In a more preferred embodiment, two spectral filters centered on 830 nm (Schott glass filters, RG830) are provided to enable the incident and re-radiated DPDW to be separated.

In FIG. 6C, the measured constant amplitude contours of the wave at 830 nm are shown as solid lines, and the measured incident amplitude contours at 780 nm are shown as dashed lines. The dashed lines demonstrate the DPDW character of the re-radiated waves. The re-radiated wave originates from within the absorbing object. As can be seen from the contours, the DPDW wavelength at 830 nm is somewhat longer than the DPDW wavelength at 780 nm. This is a function of the relatively larger diffusion coefficient for 830 nm light in Intralipid. Thus, a type of fluorescence of DPDW has occurred and the inhomogeneity is converted into a source of secondary DPDW.

An alternative embodiment to the "time-sharing apparatus" for imaging using re-radiated DPDW described by FIG. 5 is a "frequency encoded apparatus" shown in FIG. 7. In this embodiment, each source 120 is modulated by a slightly different modulation frequency, $f_i$, (i.e., $f_i$=200.00+k (0.01) MHz) and is kept on at all times. In this way, a modulation power spectrum is associated with each spatial location in the sample. By measuring the power spectrum of the re-radiated light as a function of modulation frequency with a spectrum analyzer 180, the position of object 100 can be determined using essentially the same analysis as described above with respect to the apparatus of FIG. 5. This type of imaging is similar to MRI in that a frequency spectrum emitted by an object is converted to the spatial location of the object.

Figure 8A:
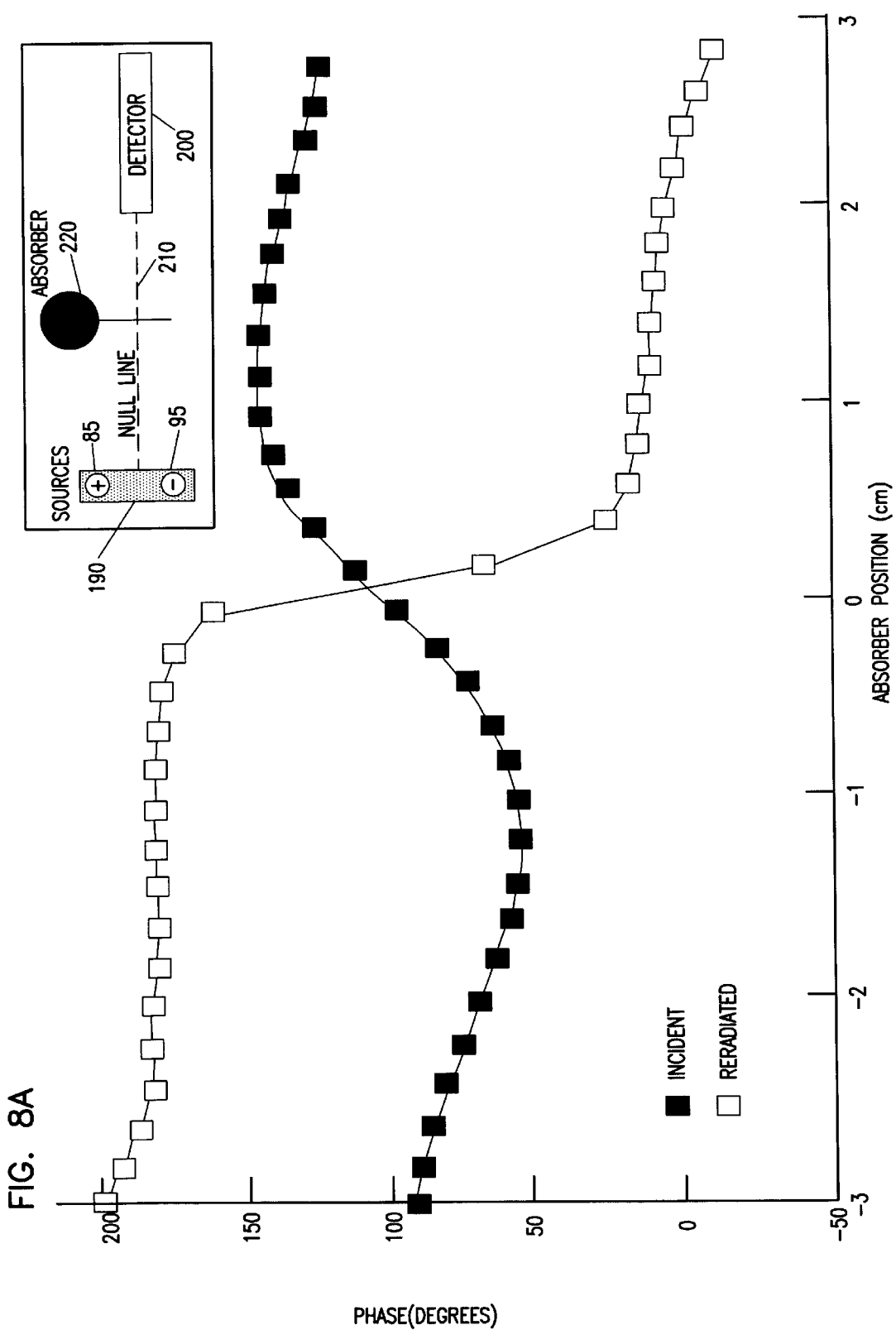
FIGS. 8A and 8B are schematic representations of "phased-array" scanning systems for imaging re-radiated diffuse photon density waves and graphs of the object's position in the turbid medium and a null line associated with the phased-array.
Figure 8B:
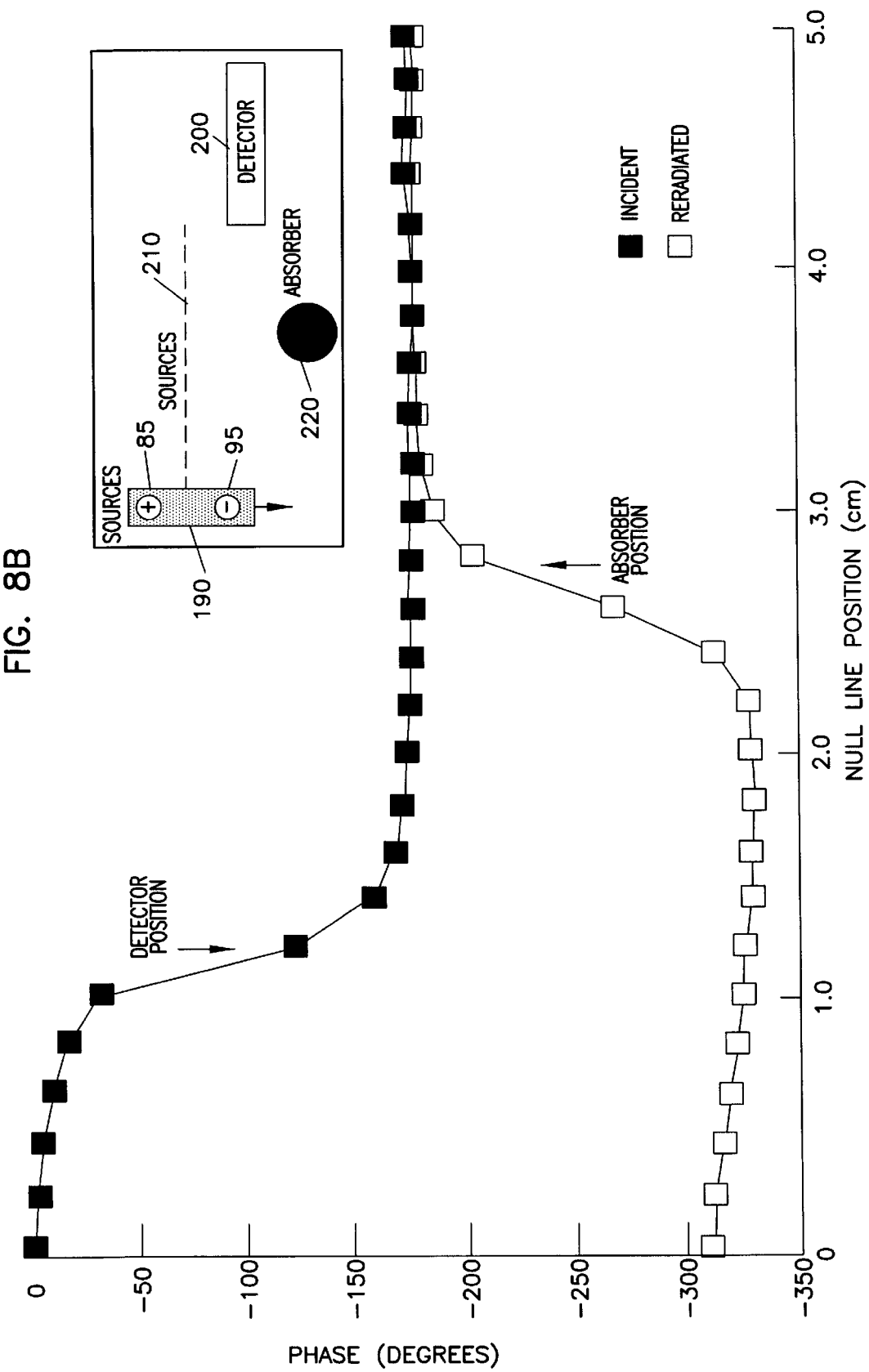

A third, alternative embodiment for imaging fluorescent objects that re-radiate DPDW is shown in FIGS. 8A and 8B. The apparatus of FIGS. 8A and 8B is qualitatively different than the time-sharing apparatus and frequency encoded apparatus of FIGS. 5 and 7 respectively, since it uses a scanning phased-array 190 and a single detector 200. Preferably, the phased-array 190 comprises two sources 85 and 95 that are substantially 180° out of phase with each other and that emit DPDW which interfere destructively to produce an amplitude null and a sharp 180° phase shift across a curve that describes this family of points called the "null line," shown schematically at 210.

By placing a detector 200 on the null line 210, and then moving an absorbing object 220 from one side of the null line 210 to the other, the object 220 will preferentially absorb light from the nearest source, and therefore distort the null line. When the absorber 220 is also a re-radiator, the complimentary effect is seen, that is, the object re-radiates more light derived from the closest source. In both measurements, the phase of the detected DPDW will undergo a 180° shift as the absorber crosses the original, undisturbed null line 210. These effects are demonstrated by the graphs of FIG. 8A. The re-radiated light displays a sharper phase transition, and a deeper amplitude null than that of the incident light, and the re-radiated wave exhibits a complimentary change as discussed above.

Interestingly, in the embodiment of FIG. 8A, the phase shift of the re-radiated light is always the same, independent of detector position. Thus, it is possible to hold the absorber 220 and the detector 200 stationary, and scan the null line 210 which will produce essentially the same results. Scanning the null line 210 can be achieved by mechanically translating the two sources 85 and 95 together.

Referring to FIG. 8B this effect is demonstrated for re-radiated light. A sharp phase shift at the location of the re-radiator 220 and null line 210 is detected. The phase transition of the incident light occurs near the position of detector 200. With knowledge of the position of the null line 210 as a function of time, a one-dimensional localization of the re-radiator can be achieved. By performing three scans down three perpendicular axes, three-dimensional localization of re-radiator 220 can be achieved. It is envisioned that the phased-array apparatus of FIGS. 8A and 8B will be simple to build and implement. Furthermore, imaging apparatus described herein will generally be much more economical to build than other imaging systems currently in use, such as MRI systems, PET systems, and CAT scanners.

Therefore, it has been demonstrated that imaging of inhomogeneities in turbid media using DPDW is both possible and practical with the methods and apparatus disclosed and claimed herein. By studying the scattering and distortion of the DPDW by inhomogeneities found therein, the inhomogeneities can be located and their sizes determined for clinical purposes. Alternatively, a fluorescent inhomogeneity can be examined by analyzing the re-radiated DPDW emitted therefrom. In accordance with the invention, it is also possible to combine the dual techniques of examining the refractive, diffractive, scattering, and fluorescent properties of the inhomogeneities to image the objects.

The techniques and apparatus of the present invention provide particularly powerful clinical tools for imaging, locating and sizing tumors in human tissue. Furthermore, the methods and apparatus claimed and disclosed herein should prove to be both economical and efficient imaging tools for clinical diagnosis.

There have thus been described certain preferred embodiments of methods and apparatus for imaging objects using diffuse light provided in accordance with the present invention. While preferred embodiments have been described and disclosed, it will be recognized by those with skill in the art that modifications are within the true spirit and scope of the invention. The appended claims are intended to cover all such modifications.

What is claimed is:

1. A system for imaging an object in a turbid medium using diffuse light comprising:
   source means for generating oscillatory diffuse photon density waves to illuminate the object;
   detection means for detecting diffuse photon density waves produced as a result of the diffuse photon density waves interacting with the object;
   processing means interfaced with the detection means for processing data corresponding to the photon density waves detected by the detection means to determine at least a position of the object; said turbid medium and the object have associated therewith at least one diffusion coefficient and the diffuse photon density waves which illuminate the object diffracts around or refracts through the object as a result of their interaction with it, thereby producing a distorted wavefront such that after the detection means detects the distorted wavefront the processing means determines the diffusion coefficient of the turbid medium and the object.

2. The system recited in claim 1 wherein the processing means constructs phase and amplitude contours corresponding to propagation of the distorted wavefront and further determines at least the position of the object from the phase and amplitude contours, thereby imaging the object.

3. The system recited in claim 2 further comprising display means interfaced with the processing means for displaying the position of the object.

4. The system recited in claim 3 wherein the source means comprises at least one laser and the detection means comprises an optical fiber interfaced with a photomultiplier tube.

5. The system recited in claim 1 wherein the object is fluorescent and the diffuse photon density waves which have a first wavelength cause the object to fluoresce, thereby producing re-radiated diffuse photon density waves having a second wavelength such that after the detection means detects the re-radiated diffuse photon density waves, the processing means can image the object.

6. The system recited in claim 5 wherein the source means comprises a plurality of lasers oriented around the object which alternately irradiate the object with the diffuse photon density waves of the first wavelength to cause the object to fluoresce.

7. The system recited in claim 6 wherein the detection means comprises an optical fiber that is placed in proximity to the object and a photomultiplier tube interfaced to the optical fiber.

8. The system recited in claim 7 further comprising switch means interfaced with each of the plurality of lasers for alternately and sequentially turning on and off each laser and radio frequency driving means interfaced through the switch means with the lasers for driving the lasers to produce the diffuse photon density waves of the first wavelength.

9. The system recited in claim 8 further comprising display means interfaced with the processing means for displaying the position of the object produced by the processing means.

10. The system recited in claim 5 wherein the source means comprises a plurality of lasers each having a spatial location with respect to the object and each laser being modulated at all times during imaging at a different frequency in a frequency range around a specified frequency, thereby producing a power spectrum associated with each spatial location around the object.

11. The system recited in claim 10 further comprising analysis means interfaced with the detection means and the processing means for analyzing the power spectrums associated with each spatial location to determine the position of the object.

12. The system recited in claim 11 further comprising display means interfaced with the processing means for displaying the image of the object.

13. The system recited in claim 5 wherein the source means comprises a phased-array.

14. The system recited in claim 13 wherein the phased-array comprises at least two lasers that are substantially one hundred and eighty degrees out of phase with each other, thereby producing the diffuse photon density waves having the first wavelength which interfere destructively to produce an amplitude null line and a one hundred and eighty degree phase shift across the null line.

15. The system recited in claim 14 wherein the phased-array scans the null line so that the processing means can produce the image.

16. A method of imaging an object in a turbid medium using diffuse light comprising the steps of:
   illuminating the object with oscillatory diffuse photon density waves;
   detecting diffuse density waves which are produced as a result of the diffuse photon density waves interacting with the object; and
   determining at least the position of the object in the turbid medium by analyzing the detected diffuse photon density waves, wherein the turbid medium and the object have associated therewith at least one diffusion coefficient and the diffuse photon density waves which illuminate the object refract around the object as a result of the interaction with it, thereby producing a distorted wavefront which is analyzed to determine the diffusion coefficient of the turbid medium and the object.

17. The method recited in claim 16 wherein the determining step comprises the steps of constructing phase contours corresponding to propagation of the distorted wavefront and determining at least the position of the object from the phase contours, thereby imaging the object.

18. The method recited in claim 17 further comprising the step of displaying the image of the object.

19. The method recited in claim 16 wherein the object is fluorescent and the diffuse photon density waves which have a first wavelength cause the object to fluoresce, thereby producing re-radiated diffuse photon density waves having a second wavelength such that detecting the re-radiated diffuse photon density waves the object to be imaged.

20. The method recited in claim 19 wherein the illuminating step comprises the step of alternately irradiating the object with at least two sources of diffuse photon density waves of the first wavelength to cause the object to fluoresce.

21. The method recited in claim 19 wherein the illuminating step comprises the step of continuously illuminating the object with at least two sources of diffuse photon density waves each having a spatial location with respect to the object, wherein each source has associated therewith a frequency in a frequency range around a specified frequency, thereby producing a power spectrum associated with each spatial location around the object.

22. The method recited in claim 19 wherein the illuminating step comprises the steps of irradiating the object with a phased-array and scanning an amplitude null line to produce the image of the object.

23. A system for imaging an object in a turbid medium comprising:
source means for illuminating the object with oscillatory diffuse photon density waves of a first specified wavelength, whereby the object will fluoresce re-radiate diffuse photon density waves of a second wavelength after being illuminated with the oscillatory diffuse photon density waves of the first specified wavelength;
detection means for detecting the re-radiate diffuse photon density waves of the second wavelength; and
processing means interfaced with the detection means for processing data corresponding to the re-radiated diffuse photon density waves of the second wavelength to determine at least the position of the object in the turbid medium.

24. The system recited in claim 23 wherein the source means comprises a plurality of lasers oriented around the object which alternately irradiated the object with the diffuse photon density waves of the first wavelength to cause the object to fluoresce.

25. The system recited in claim 24 wherein the detection means comprises an optical fiber that is placed in proximity to the object and a photomultiplier tube interfaced to the optical fiber.

26. The system recited in claim 25 further comprising switch means interfaced with each of the plurality of lasers for alternately and sequentially turning on and off each laser and radio frequency driving means interfaced through the switch means with the lasers for driving the lasers to produce the diffuse photon density waves of the first wavelength.

27. The system recited in claim 26 further comprising display means interfaced with the processing means for displaying the image of the object produced by the processing means.

28. The system recited in claim 23 wherein the source means comprises a plurality of lasers each having a spatial location with respect to the object and each laser is modulated at all times during imaging at a different frequency in a frequency range around a specified frequency, thereby producing a power spectrum associated with each spatial location around the object.

29. The system recited in claim 28 further comprising analysis means interfaced with the detection means and the processing means for analyzing the power spectrums associated with each spatial location to determine the position of the object.

30. The system recited in claim 29 further comprising display means interfaced with the processing means for displaying the image of the object.

31. The system recited in claim 23 wherein the source means comprises a phased-array.

32. The system recited in claim 31 wherein the phased-array comprises at least two lasers that are substantially one hundred and eighty degrees out of phase with each other, thereby producing the diffuse photon density waves having the first wavelength which interfere destructively to produce an amplitude null line and a one hundred and eighty degree phase shift at points equidistant from the lasers.

33. The system recited in claim 32 wherein the phased-array scans the null line so that the processing means can produce the image.

34. A method of imaging an object in a turbid medium comprising the steps of:
illuminating the object with oscillatory diffuse photon density waves of a first specified wavelength;
allowing the object to fluoresce, thereby reradiating a diffuse photon density waves having a second wavelength;
detecting the re-radiated diffuse photon density waves having the second wavelength; and
analyzing the photon density waves having the second wavelength to determine at least the position of the object based on its image in the turbid medium.

35. The method recited in claim 34 wherein the illuminating step comprises the step of alternately irradiating the object with at least two sources of diffuse photon density waves of the first wavelength to cause the object to fluoresce.

36. The method recited in claim 34 wherein the illuminating step comprises the step of continuously illuminating the object with at least two sources of diffuse photon density waves each having a spatial location with respect to the object, wherein each source has associated therewith a frequency in a frequency range around a specified frequency, thereby producing a power spectrum associated with each spatial location around the object.

37. The method recited in claim 34 wherein the illuminating step comprises the steps of irradiating the object with a phased-array and scanning an amplitude null line to produce the image of the object.

38. A system for imaging an object in a turbid medium wherein the turbid medium and object have a diffusion coefficient associated therewith comprising:
source means for illuminating the object with oscillatory diffuse photon density waves, whereby a distorted wavefront of diffuse photon density waves is created by refraction of the oscillatory diffuse photon density waves refracting around the object;

detection means for detecting the distorted wavefront of diffuse photon density waves refracted around the object;

processing means interfaced with the detection means for constructing phase contours corresponding to propagation of the distorted wavefront of diffuse photon density waves to determine at least the position of the object in the turbid medium; and display means interfaced with the processing means for displaying the image of the object.

39. The system recited in claim 38 wherein the source means comprises at least one laser and the detection means comprises an optical fiber interfaced with a photomultiplier tube.

40. A method of imaging an object in a turbid medium wherein the turbid medium and the object have a diffusion coefficient associated therewith comprising the steps of:

illuminating the object with oscillatory diffuse photon density waves;

allowing the diffuse photon density waves to refract around the object throughout the turbid medium thereby producing a distorted wavefront of diffuse photon density waves;

detecting the distorted wavefront of diffuse photon density waves;

analyzing the distorted wavefront of diffuse photon density waves to determine at least the position of the object in the turbid medium utilizing the steps of constructing phase contours corresponding to propagation of the distorted wavefront and determining at least the position of the object from the phase contours, thereby imaging the object; and displaying the image of the object.

* * * * *